United States Patent
Toyoshima et al.

(10) Patent No.: US 6,186,993 B1
(45) Date of Patent: *Feb. 13, 2001

(54) WRAPPING CONSTRUCTION OF ABSORBENT ARTICLE

(75) Inventors: Yasuo Toyoshima; Mitsugu Hamajima; Minoru Nakanishi; Kimiko Isobe, all of Tochigi-ken (JP)

(73) Assignee: Kao Corporation, Tokyo (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/824,124

(22) Filed: Mar. 26, 1997

(30) Foreign Application Priority Data

Mar. 26, 1996 (JP) .................................................. 8-070756

(51) Int. Cl.[7] .............................. A61F 13/15; A61B 17/06
(52) U.S. Cl. ...................... 604/385.02; 604/387; 206/438
(58) Field of Search ................................ 604/385.1, 386, 604/387, 389, 391, 385.01, 385.02, 385.03, 385.04, 385.05; 206/438, 440

(56) References Cited

U.S. PATENT DOCUMENTS

| | | | |
|---|---|---|---|
| 5,088,993 | * 2/1992 | Gaur | 604/386 |
| 5,201,727 | * 4/1993 | Nakanishi et al. | 604/387 |
| 5,413,568 | * 5/1995 | Roach et al. | 604/389 |
| 5,478,336 | * 12/1995 | Pigneul | 604/389 |
| 5,484,636 | * 1/1996 | Berg et al. | 604/389 |
| 5,569,228 | * 10/1996 | Byrd et al. | 604/387 |
| 5,569,230 | * 10/1996 | Fisher et al. | 604/387 |
| 5,683,377 | * 11/1997 | Mizutani | 604/387 |
| 5,792,131 | * 8/1998 | Mizutani | 604/385.1 |
| 5,800,654 | * 9/1998 | Davis et al. | 604/387 |
| 5,954,201 | * 9/1999 | Finch et al. | 206/440 |
| 5,993,430 | * 11/1999 | Gossens et al. | 604/387 |

FOREIGN PATENT DOCUMENTS

| | | |
|---|---|---|
| 2 273 279 | * 6/1994 | (GB) . |
| 5506799 | 10/1993 | (JP) . |
| 739820 | 7/1995 | (JP) . |

* cited by examiner

*Primary Examiner*—John G. Weiss
*Assistant Examiner*—Carie Mager
(74) *Attorney, Agent, or Firm*—Birch, Stewart, Kolasch & Birch, LLP

(57) ABSTRACT

A wrapping construction of an absorbent article includes a sanitary napkin 2 as an absorbent article including a body 3, and a pair of left and right wing portions 4,4 disposed on opposing left and right sides of the body 3. The body 3 is provided on a skin non-contacting surface 32 side thereof with a body adhesive portion 37. Each of the wing portions 4,4 is provided on a skin non-contacting surface 32 side thereof with a wing adhesive portion 41. The construction further includes a wrapping material 5 for individually wrapping the sanitary napkin. The method of making the wrapping construction includes the steps of: the wing portions 4,4 being folded towards a skin contacting surface side 31 of the body 3; the body adhesive portion 37 being in contact with and peelably adhered to an inner surface 54 of the wrapping material 5; the wrapping material 5 being allowed to extend at opposing left and right side edge portions 52, 52 and a front end edge 51 thereof outwardly of opposing side edges 3b, 3b and a front end edge 3a of the body 3, respectively; the sanitary napkin 2 and the wrapping material 5 being folded by gradually folding from rear end edge sides 3c thereof with the skin contacting surface 31 sides facing inwardly; and an outer surface 55 of the wrapping material 5, with which the end edge side 3c of the body 3 being in contact, being peelably adhered to said wing adhesive portions 37.

13 Claims, 3 Drawing Sheets

WRAPPING CONSTRUCTION OF ABSORBENT ARTICLE

BACKGROUND OF THE INVENTION

1. Field of the Invention

This invention relates to a wrapping construction of an absorbent article, and more particularly to a wrapping construction of an absorbent article, capable of individually compactly wrapping an absorbent article having a pair of wing portions without degrading the slip-preventive properties while providing an absorbent article which is easy to take out.

2. Description of Related Art

Absorbent articles having a pair of wing portions on opposing sides of a sanitary napkin body are widely used.

In a conventional wrapping construction for individually wrapping a sanitary napkin having wings, peelable materials separate from an individual-wrapping material are needed, so that adhesive portions of the body and the wings can be covered with the peelable materials.

Due to the conventional design, it is required for the user of such a conventional wrapping construction to take the trouble of removing the peelable materials provided to cover the adhesive portion of the body and the adhesive portion of the wing portions when the user wears a sanitary napkin. Moreover, the peelable materials thus removed remain as waste products. In addition, the adhesive portion of the body and the adhesive portions of the wing portions are left uncovered from the time the peelable materials are removed to the time the adhesive portions are attached to an undergarment such as sanitary shorts or the like. Besides, since the peelable materials are left as waste materials, handling difficulties occur. Therefore, handling of the sanitary napkin is likely to be completed incorrectly. As a consequence, there is a high probability that the adhesive portion of the body and the adhesive portions of the wing portions are accidentally attached together. This eventually makes it difficult for the absorbent article to fully perform as designed in many cases. The problems so far described can be hindrances for providing a favorable leak-preventive absorbent article.

For the purposes of obviating the above problems, various proposals have been made with respect to a wrapping construction of an absorbent article.

One such proposal is made by JPT. 506799/1993, in which a pair of wing portions are provided with adhesive portions in a wrapping construction of a sanitary napkin. The wing portions are folded back towards a topsheet side and the adhesive portion on each wing portion is protected by a peelable paper.

However, this conventional wrapping construction has the following shortcomings: the peelable papers protecting the adhesive portions of the wing portions must be removed before the sanitary napkin is worn. Moreover, since the peelable papers remain as waste products after removal, the problem of handling difficulty is left unsolved. Furthermore, since separate materials such as peelable papers are necessary to the conventional wrapping construction, the manufacturing process becomes complicated and productivity worsens while the cost is increased.

Japanese Laid-Open Utility Model Application No. 39820/1995 also proposes a wrapping construction of a sanitary napkin. A pair of wing portions are folded upon a topsheet of the sanitary napkin and longitudinal opposing end portions of the wrapping material are allowed to extend outwardly of longitudinal opposing end portions of the sanitary napkin. The extending wrapping material is folded back at one end edge thereof upon the topsheet so that adhesive portions of the wing portions may be protected by peelable portions disposed on the outer surface of the extending wrapping material.

However, in this wrapping construction, since it is necessary that one edge portion of longitudinal end of the wrapping material is allowed to extend outwardly of a corresponding one longitudinal end edge portion of the sanitary napkin in order to protect the adhesive portions of the wing portions, a large quantity of wrapping material is required. Therefore, the cost is increased. Moreover, since the wrapping construction is not compact, it is inconvenient to carry and therefore, portability is poor.

In the present specification, "edge portion" means an end edge portion in the longitudinal end of the wrapping material or the absorbent article, and is also referred to as "longitudinal end edge portion" hereinafter.

SUMMARY OF THE INVENTION

It is, therefore, an object of the present invention to provide a wrapping construction of an absorbent article which is easy to wear and handle, while the efficiency of the like antileak property is not degraded. With this invention peelable papers separate from the wrapping material are unnecessary. This invention increases productivity where the quantity of material to be used is comparatively small. The invention can individually and compactly wrap an absorbent article such a sanitary napkin.

As a result of investigation made by the present inventors for the purposes of solving the above-mentioned problems, they found out that the resolution of the above-mentioned problems can be achieved by wrapping an absorbent article such as a sanitary napkin, where a wrapping material is integrally folded three or more times.

The present invention has been accomplished based on the above finding. According to the present invention, there is essentially provided a wrapping construction of an absorbent article comprising an absorbent article including a body, and a pair of left and right wing portions disposed on opposing left and right sides of said body; the body being provided on a side of a surface thereof not contacting skin with an adhesive portion of the body; each of the wing portions being provided on a side of a surface thereof not contacting skin with an adhesive portion each of the wing portions; and a wrapping material for individually wrapping the absorbent article; the wing portions being folded towards a skin contacting surface side of the body; the adhesive portion of said body being in contact with and peelably adhered to an inner surface of the wrapping material; the wrapping material being allowed to extend at opposing left and right side edge portions and a front end edge thereof outwardly opposing side edges and a front end edge of the body, respectively; the absorbent article and the wrapping material being folded by gradually folding from edge of rear end sides thereof with the skin contacting surface sides facing inwardly; and an outer surface of the wrapping material which contacts the edge of rear end side of the body is peelably adhered to the adhesive portion each of wing portions.

In the present specification, "a surface not contacting skin" means a surface which does not contact the skin when a user wears the absorbent article but contacts a surface of the shorts, and is also referred to as "skin non-contacting surface" hereinafter.

In addition, "adhesive portion of the body" and "adhesive portion of the wing portion" mean adhesive portions provided on the body and the wing portion respectively, and are referred to as "body adhesive portion" and "wing adhesive portion", respectively hereinafter.

Further, "edge of rear end" means an edge portion in the rear end of the body or the wrapping material, and is also referred to as "rear end edge" hereinafter.

Furthermore, "skin contacting surface" means a surface which directly contacts the skin when a user wears the absorbent article.

Also, according to the present invention, there is provided the above-mentioned wrapping construction of an absorbent article. The absorbent article is adhered to the wrapping material and is longitudinally divided into the following: a wing folding portion where the wing portions are folded; a front portion located forwardly of the wing folding portion; a rear center portion located backwardly of the wing folding portion; and a rear end portion located backwardly of the rear center portion; the absorbent article and the wrapping material are integrally folded together in such a way to form a quadruplicate construction.

Further, according to the present invention, there is provided the above-mentioned wrapping construction of an absorbent article, wherein the wrapping material is sealed at the opposing left and right side edge portions and the front end edge.

A wrapping construction of an absorbent article according to the present invention is designed such that productivity is high, in which the quantity of material to be used is small, and in which an absorbent article such as a sanitary napkin can be individually compactly be wrapped.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

A wrapping construction of a sanitary napkin as one embodiment of a wrapping construction of an absorbent article according to the present invention will now be described in detail with reference to the accompanying drawings.

Figure 1:
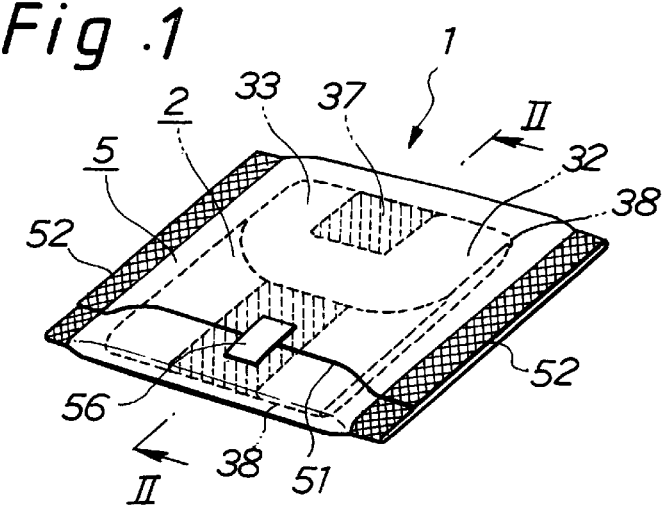
FIG. 1 is a perspective view showing one embodiment of a wrapping construction of a sanitary napkin as a wrapping construction of an absorbent article according to the present invention.
Figure 2:
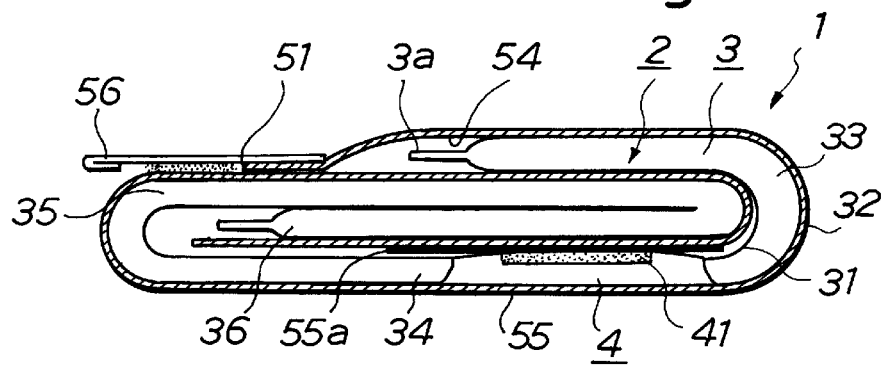
FIG. 2 is a sectional view taken on line II—II of FIG. 1.

A wrapping construction 1 of a sanitary napkin according to one embodiment of FIGS. 1 and 2 comprises a sanitary napkin 2 (see FIG. 3) including a body 3, and a pair of left and right wing portions 4,4 disposed on opposing left and right sides of the body 3. The body 3 is provided on a skin non-contacting surface 32 side thereof with a body adhesive portion 37. Each of the wing portions 4,4 being provided on a skin non-contacting surface 32 side thereof with a wing adhesive portion 41, and a wrapping material 5 for individually wrapping the sanitary napkin 2.

Figure 3:
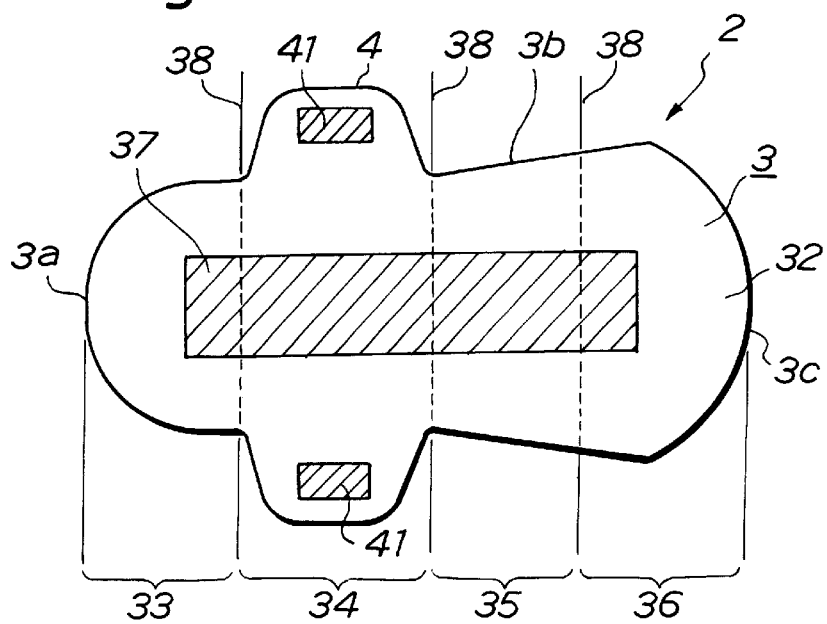
FIG. 3 is a perspective view showing a skin non-contacting surface side (i.e., the surface side which does not contact the user's skin) of a sanitary napkin which is employed in this embodiment.

More specifically, as shown in FIG. 3, the sanitary napkin 2 employed in the wrapping construction 1 is an ordinary sanitary napkin, in which the skin contacting surface 31 is formed of a liquid permeable sheet member and the skin contacting surface 32 is formed of a liquid impermeable sheet member, which has a liquid retentive member (not shown) interposed between the skin contacting surface 31 and the skin non-contacting surface 32, and in which the body adhesive portion 37 and the wing adhesive portions 41 are also formed of an ordinary adhesive agent. The wing portions 4,4 are formed offset towards the front end edge sides of the napkin.

The body adhesive portion 37 is disposed on the skin non-contacting surface 32 over almost all the area thereof. The expression "over almost all the area thereof" used here refers to an arrangement wherein the body adhesive portion 37 may be provided at any portions of a front portion 33, a wing folding portion 34, a rear center portion 35 and a rear end portion 36 as later described.

Figure 4:
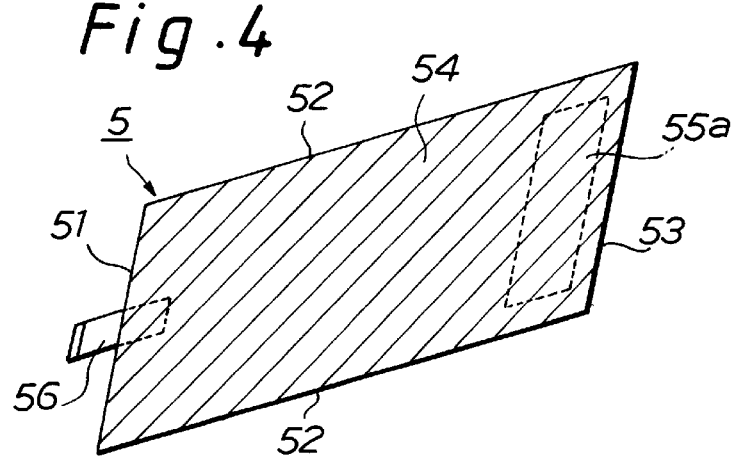
FIG. 4 is a perspective view showing an inner surface side of a wrapping material employed in this embodiment.

As shown in FIG. 4, the wrapping material 5 has a generally rectangular configuration. It is provided at a front end portion thereof with a conventional tab tape 56 for sealing the wrapping construction. Also, the wrapping material 5 of the present invention is required to have peelability where an entire area of an inner surface 54 of the wrapping material 5 or the area with which the body adhesive portion 37 is in contact and its vicinity is subjected to peeling treatment. It is not absolutely necessary for the present invention that the entire area of the inner surface 54 is subjected to peeling treatment. It suffices that only a part of the inner surface 54, for example, only the area excluding the peripheral edge portion of the inner surface 54 is subjected to peeling treatment.

With respect to the wrapping material 5, known suitable materials may be used without any particular limitation. Concrete examples may include polypropylene, polyester, polyethylene, polyvinyl-alcohol, non-woven fabric or paper, and composite material thereof, all having a thickness of from 5 to 50 $\mu$m.

The peeling treatment may be carried out using any suitable means known without any particular limitation. For example, the peeling treatment can be carried out either by applying a peeling treatment agent or by adhering a peelable tape, a peelable paper, a non-woven fabric subjected to peeling treatment, a polyethylene laminated paper subjected to peeling treatment, or a polyethylene film subjected to peeling treatment, to the entire area of the inner surface of the wrapping material 5. The peeling treatment agent or a peeling agent component applied the peelable tape and the peelable paper thereof are preferably selected from silicon resin series, fluororesin series, octadecilisocyanate series, and the like. It is particularly preferable that the peeling treatment is carried out by applying a selected one of the silicon resin series as the peeling agent component. The peeling agent is dried by heating or by irradiating ultraviolet rays or the like so as to be polymerized, or by spraying it, to thereby form a thin film.

Furthermore, a peeling means obtained by providing a thin polyolefin film or a polyester film subjected to peeling treatment to the wrapping material 5 using heating or ultrasonic means has appropriate stiffness, permits the wrapping material 5 to be easily open and has the advantage of productivity because of its excellent heat-resisting properties.

As shown in FIGS. 1 and 2, in the wrapping construction 1 according to the embodiment, the wing portions 4,4 are folded towards the skin contacting surface 31 side and the body adhesive portion 37 is in contact with and is peelably adhered to an inner surface 54 of the wrapping material 5. The wrapping material 5 is allowed to extend at opposing left and right side edge portions 52, 52 and a front end edge 51 thereof outwardly of opposing side edges 3b, 3b and a front end edge 3a of the body 3, respectively. The sanitary napkin 2 and the wrapping material 5 is folded by gradually folding from rear end edge 3c sides thereof with the skin contacting surface 31 sides facing inwardly. An outer surface of the wrapping material 5 which contacts the end edge side of the body 3 is peelably adhered to the wing adhesive portions 41.

Figure 5:
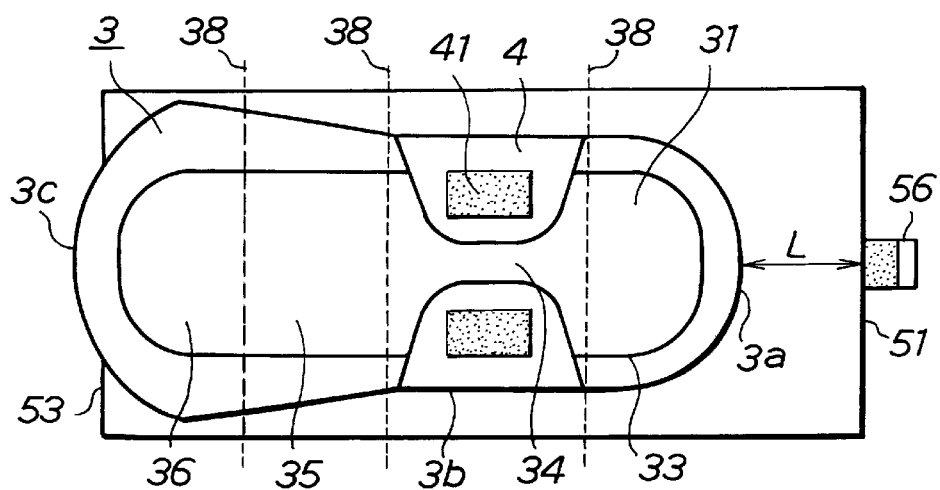
FIG. 5 is a plan view (development view of the wrapping construction) showing the sanitary napkin being in contact with the wrapping material.
Figure 6:
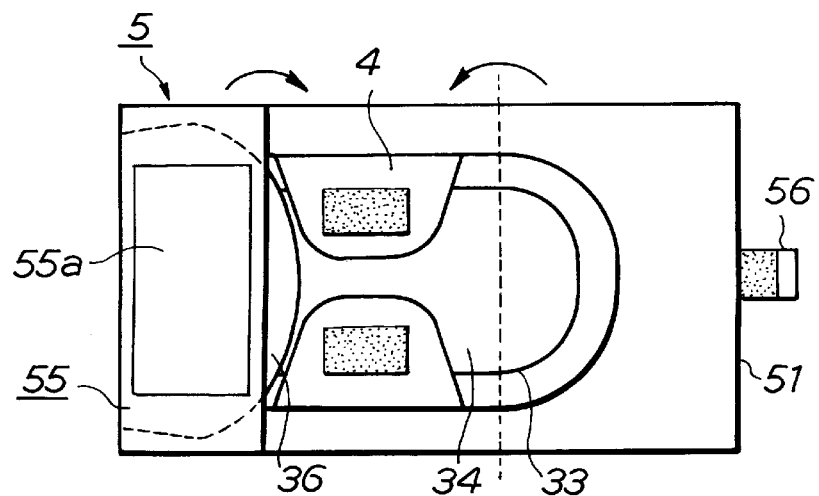
FIG. 6 is a plan view showing the sanitary napkin, a rear end portion of which is folded back.

More specifically, as shown in FIGS. 2, 5 and 6, the sanitary napkin 2 adhered to the wrapping material 5 is longitudinally divided by folds 38 into portions comprising: a wing folding portion 34 where the wing portions 4,4 are folded, a front portion 33 located forwardly of the wing folding portion 34, a rear center portion 35 located backwardly of the wing folding portion 34, and a rear end portion 36 located backwardly of the rear center portion 35. The sanitary napkin 2 and the wrapping material 5 are integrally folded together in such a way to form a quadruplicate layer construction.

Here, as shown in FIGS. 2 through 4, the wing folding portion 34 is a portion where the wing portions 4,4 are located on the skin contacting surface 31 because the wing portions 4,4 are folded. The term "forwardly" of the wing folding portion 34 refers to a location offset more forwardly of the user than the wing folding portion 34 when in use, and the term "backwardly" refers to a location offset more backwardly of the user than the wing folding portion 34 when in use. Accordingly, the front portion 33 is a part of the sanitary napkin 2 which is located most forwardly of the user when in use, and the rear end portion 36 is a part of the sanitary napkin 2 which is located most backwardly of the user when in use.

The term "quadruplicate layer construction" refers, as shown in FIG. 2, to a state that when the sanitary napkin 2 and the wrapping material 5 protecting the body adhesive portion 37 of the sanitary napkin 2 are regarded as one integral layer which is folded in four.

In this embodiment, the inner surface 54 of the wrapping material 5, with which the body adhesive portion 37 is in contact, is subjected to peeling treatment. Specifically, the inner surface 54 of the wrapping material 5, with which the body adhesive portion 37 is in contact, is formed by adhering a peelable paper to the wrapping material 5 through an adhesive agent. By this, the inner surface 54 is subjected to peeling treatment.

Also, as shown in FIGS. 2 and 5, since the wing portions 4,4 are folded towards the skin contacting surface 31 side, the wing adhesive portions 41 are located on the outer surface of the skin contacting surface 31 in such a way to face the skin contacting surface 31.

Almost all the areas of the skin non-contacting surface 32 is adhered to the wrapping material 5 such that the entire surface of the body adhesive portion 37 on the skin non-contacting surface 32 is protected by the wrapping material 5. That is, the expression "almost all the areas" means that the entire surface of at least the body adhesive portion 37 is covered by the wrapping material 5.

Also, the outer surface of the wrapping material 5, with which the rear end edge 3c side of the body 3 is in contact, is subjected to peeling treatment. Specifically, the outer surface of the wrapping material 5, with which the rear end edge 3c side of the body 3 is in contact, is formed by adhering a peelable paper to the wrapping material 5 through an adhesive agent. By this, the outer surface of the wrapping material 5 is subjected to peeling treatment.

A part of the outer surface 55 of the wrapping material 5, with which the rear end portion 36 is in contact, is formed with a peelably treated portion 55a. The peelably treated portion 55a is formed by applying a peeling treatment to that part of the outer surface 55. Referring to FIG. 4, it can be clearly understood that the inner surface 54, which has an entire surface subjected to peeling treatment, has an area which is substantially greater than the area of the peelably treated area 55a.

The peeling treatment is made in the same manner as the aforementioned peeling treatment applied to the inner surface 54 of the wrapping material 5. In this embodiment, the peelable paper is adhered through an adhesive agent. In the alternative, a peelable tape may be adhered for the purpose of the peeling treatment or a polyethylene laminated paper subjected to peeling treatment may be adhered. While the peelable paper used is not particularly limited, the peelable paper is formed at least by applying the peeling agent component thereto. A suitable known peelable paper may be used. The adhesive agent is not particularly limited, either.

The length L of that part of the front end edge 51 which extends outwardly of the front end edge 3a of the absorbent article (see FIG. 5) is preferably from 0.1 to 5 cm.

If the front end edge 51 extends outwardly, there is no need that the rear end edge 53 side extends outwardly. In this embodiment, the rear end edge 53 is designed to be shorter than the rear end edge 3c of the sanitary napkin 2. The opposing left and right side edges of the wrapping material 5 also extend outwardly of opposing side edges of the sanitary napkin 2.

The wrapping material 5 is sealed at its opposing left and right side edge portions 52, 52 and at its front end edge 51.

The wrapping material 5 is sealed at its opposing left and right side edge portions 52 by heat sealing. A seal member is disposed at the front end edge 51 of the wrapping material 5. In this embodiment a tab tape 56 is employed as the seal member. The front end edge 51 is sealed by the tab tape 56. Also, the wrapping material 5 is heat sealed at its opposing left and right side edge portions 52. However, in order to facilitate easy opening, perforations may be formed along the area where the heat sealing is applied.

Since the wrapping construction of the sanitary napkin 2 according to this embodiment is constituted in the manner as described above, there is no worry that extra wastes are produced. Even a large sanitary napkin 2 for night use, etc. can be packed compactly. Accordingly, the wrapping construction is compact. This makes it easy to carry with. Moreover, such a napkin 2 can easily be fitted to the body of the user because when taken out by opening the wrapping construction, the sanitary napkin 2 has the four-fold marks in configuration.

Furthermore, since it has a construction easy to manufacture as later described, productivity is high and cost is low.

The wrapping construction 1 of the sanitary napkin 2 can easily be manufactured in the following manner.

First, as shown in FIG. 5, the skin non-contacting surface 32 of the sanitary napkin 2 with the wing portions 4,4 folded is brought into contact with the wrapping material 5 whose inner and outer surfaces 54 and 55a are subjected to peeling treatment by preliminarily joining a peelable paper to a predetermined location, such that the body adhesive portion 37 of the sanitary napkin 2 is adhered to the inner surface 54 of the wrapping material 5. Then, as shown in FIG. 6, the rear end portion 36 is folded back upon the rear center portion 35 in unison with the wrapping material 5, and the rear center portion 35 with the rear end portion 36 folded back thereon is folded back upon the wing folding portion 34 in unison with the wrapping material 5. Thereafter, the front portion 33 is folded back upon the wing folding portion 34 upon which the rear center portion 35 and the rear end portion 36 are folded, in unison with the wrapping material 5. Lastly, the opposing left and right side edges of the wrapping material 5 are heat sealed and cut, and the tab tape 56 is adhered to the front end edge 51. By sealing the opposing left and right side edge portions 52 and the front end edge 51 in this way, a wrapping construction of a sanitary napkin according to this embodiment can be obtained.

It is not always necessary that the peelable paper is preliminarily joined to the outer surface of the wrapping material 5. Instead, the peelable paper may be joined to the outer surface of the wrapping material 5 at one stage of the manufacturing process of the wrapping construction as mentioned hereinafter.

In order to protect the adhesive portions 41 of the wing portions 4,4 on the skin contacting surface 31 and to stabilize the configuration of the wing folding portion 34 during transportation, after ensuring that the wing adhesive portions 41 are protected by the peelable paper contacted with the wing portions 4,4, an adhesive agent is applied to the back sides of the peelable papers or the outer surface of the wrapping material 5 which contacts the rear end portion 36. Subsequently, the rear center portion 35 with the rear end portion 36 folded back thereupon is folded upon the wing folding portion 34 in unison with the wrapping material 5. By doing this, the wrapping material 5 and the peelable paper can be jointed together through the adhesive agent.

For use of the sanitary napkin 2, the tab tape 56 is detached and the heat sealed portions at the opposing left and right side edge portions 52 are peeled off (in case perforations are formed, the side edge portions 52 are peeled off along the perforations), such that the front portion 33, the rear center portion 35 and the rear end portion 36 are opened in order. As a consequence, the wrapping construction 1 is opened and the sanitary napkin 2 are ready to be taken out for use.

Another embodiment of a wrapping construction of a sanitary napkin as a wrapping construction of an absorbent article according to the present invention shown in FIG. 7 will now be described.

Those points which are not described in detail are the same as the embodiment shown in FIGS. 1 through 6.

Figure 7:
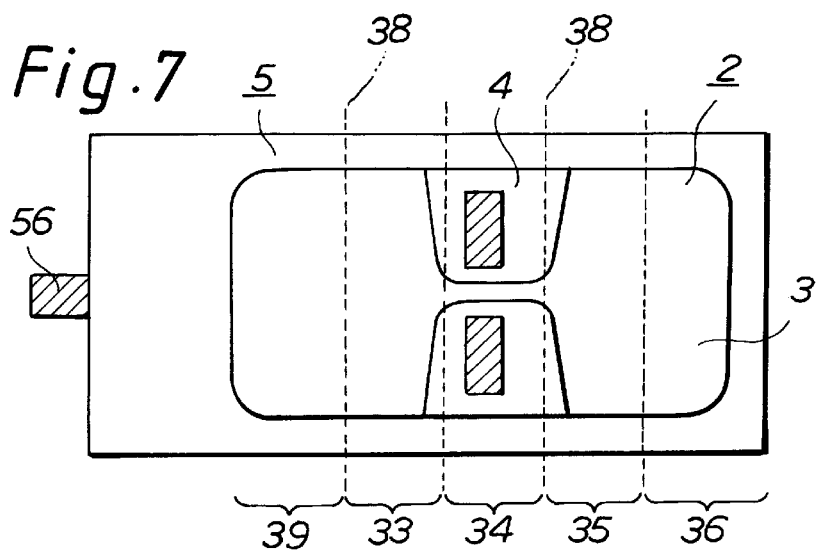
FIG. 7 is a development view (corresponding to FIG. 5) showing another embodiment of a wrapping construction of a sanitary napkin as a wrapping construction of an absorbent article according to the present invention.

The wrapping construction 1 of a sanitary napkin according to the embodiment of FIG. 7 has a further division of a front end portion 39 located forwardly of the front portion 31. By folding back the sanitary napkin 2 and the wrapping material 5 upon the front end portion 39 in unison in order of the rear end portion 36, the rear center portion 35, the wing folding portion 34 and the front portion 33, a quintuple layer construction can be obtained. The remaining points are the same as the embodiment of FIGS. 1 through 6.

Next, another embodiment of a wrapping construction of a sanitary napkin according to the present invention will be described with reference to FIGS. 8 and 9. Those points which are not described in detail are the same as the embodiment shown in FIGS. 1 through 6.

Figure 8:
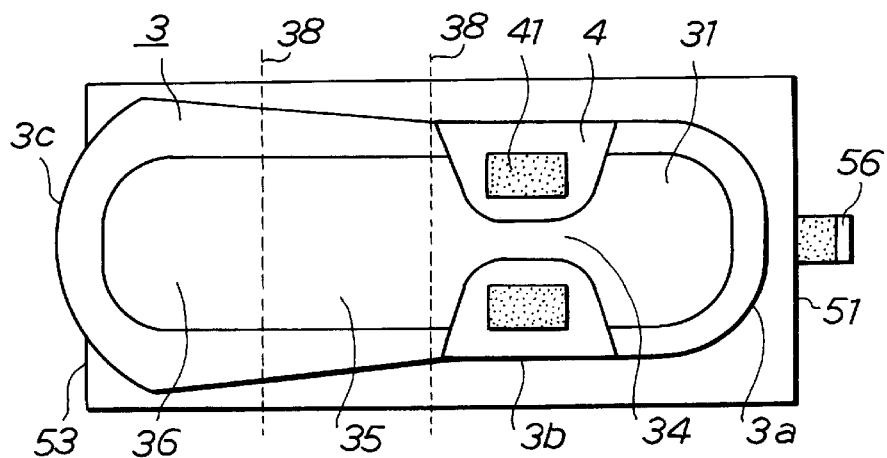
FIG. 8 is a development view (corresponding to FIG. 5) showing a further embodiment of a wrapping construction of a sanitary napkin as a wrapping construction of an absorbent article according to the present invention.
Figure 9:
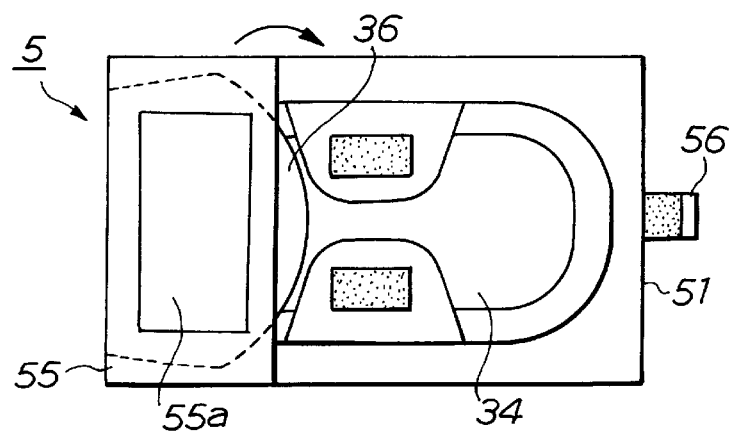
FIG. 9 is a plan view (corresponding to FIG. 6) showing the sanitary napkin, a rear end portion of which is folded back.

The wrapping construction of a sanitary napkin shown in FIGS. 8 and 9 is divided into three sections; a wing folding portion 34, a rear center portion 35 and a rear end portion 36. In the sanitary napkin of this embodiment, the wing portions 4,4 are offset forwardly. By folding back the sanitary napkin 2 and the wrapping material 5 upon the wing folding portion 34 in unison in order to the rear end portion 36 and the rear center portion 35, a triple-layer construction can be obtained. The remaining points are the same as the embodiment of FIGS. 1 through 6. As seen in the foregoing, the number of layers is not particularly limited, as long as the number is at least three or more.

The wrapping construction of the present invention is not limited to the above embodiments. It can be modified in various ways without departing from the scope of the present invention.

For example, a portion 55 of the wrapping material 5, with which the rear end portion 36 is in contact, may be formed of an another separate member.

Also, the wing portions 4,4 may be located generally in the longitudinally central area of the sanitary napkin 2.

The wrapping construction of the present invention may be applied to many other absorbent articles such as incontinent pads.

Also, the wrapping material on the rear end portion side may be designed to extend outwardly of the rear end edge of the absorbent article.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A wrapping construction of an absorbent article comprising:

an absorbent article including a body;

a pair of left and right wing portions disposed on opposing left and right lateral sides of said body, said body being provided with an adhesive portion on a side of a surface thereof not contacting skin, each of said wing portions being provided with an adhesive portion on said side of said body not contacting skin;

a wrapping material for individually wrapping said absorbent article, said wrapping material includes a planar sheet with an inner surface and an outer surface, said inner surface and outer surface define respective planar sides of said wrapping material which are relatively opposite to one another, said inner surface includes a first peeling treatment layer having a first area, said outer surface includes a second peeling treatment layer having a second area, said second area being located opposite a location of a rear end portion of said body when said absorbent article and said wrapping material are oriented in a flattened, unfolded state, said first area is substantially greater than said second area, said wing portions being folded towards a skin contacting surface side of said body, said adhesive portion of said body being in contact with and peelably adhered to said inner surface and said first peeling treatment layer, said wrapping material extending at opposing left and right side edge portions of opposing side edges of said body; and a front end edge of said wrapping material extending outwardly of a front end edge of said body, said absorbent article and said wrapping material being folded by gradually folding from an edge of rear end sides thereof with said skin contacting surface sides facing inwardly; said outer surface of said wrapping material with said second area contacts and is peelably adhered to said wing adhesive portions when said absorbent article and said wrapping material are in a folded condition, whereby separate peelable papers protecting said adhesive portions of said wing portions are eliminated which in turn substantially increases manufacturing efficiency while said wrapping material compactly wraps said absorbent article.

2. The wrapping construction of an absorbent article according to claim 1, wherein said absorbent article adhered to said wrapping material is longitudinally divided by folds into portions comprising;

a wing folding portion where said wing portions are folded;

a front portion located forwardly of said wing folding portion;

a rear center portion located backwardly of said wing folding portion; and a rear end portion located backwardly of said rear center portion, said absorbent article and said wrapping material are integrally folded together to form at least quadruplicate layer construction.

3. The wrapping construction of an absorbent article according to claim 1, wherein said wrapping material is sealed at the opposing left and right side edge portions and the front end edge.

4. The wrapping construction of an absorbent article according to claim 3, wherein a seal member is disposed at the front end edge of said wrapping material.

5. The wrapping construction of an absorbent article according to claim 4, wherein said seal member is a tab tape.

6. The wrapping construction of an absorbent article according to claim 1, wherein the inner surface of said wrapping material having said first peeling treatment layer contacts said adhesive portion of said body and is formed by adhering a peelable paper to said wrapping material through an adhesive agent.

7. The wrapping construction of an absorbent article according to claim 1, wherein the outer surface of said wrapping material having said second peeling treatment layer is formed by adhering a peelable paper to said wrapping material through an adhesive agent.

8. The wrapping construction of an absorbent article according to claim 2, wherein said front portion comprises a fold to form a subportion, and the absorbent article and said wrapping material are integrally folded together to form a quintuple layer construction.

9. The wrapping construction of an absorbent article according to claim 1, wherein said absorbent article adhered to said wrapping material is longitudinally divided by folds into portions comprising;

a wing folding portion wherein wing portions are offset forwardly;

a rear center portion located backwardly of said wing folding portion; and a rear end portion located backwardly of said rear center portion, wherein the absorbent article and said wrapping material are integrally folded together to form a triple layer construction.

10. The wrapping construction of an absorbent article according to claim 1, wherein a rear end edge of said body extends beyond a rear end edge of said wrapping material.

11. The wrapping construction of an absorbent article according to claim 1, wherein a rear end edge of said body extends beyond a first of the folds and said second area is located between a rear end edge of said wrapping material and said first fold.

12. The wrapping construction of an absorbent article according to claim 1, wherein a rear end edge of said body is folded in a first fold into contact with a rear portion of said body.

13. The wrapping construction according to claim 1, wherein both said absorbent article and said wrapping material are folded with each fold.

* * * * *